US009878080B2

(12) United States Patent
Kaiser et al.

(10) Patent No.: US 9,878,080 B2
(45) Date of Patent: Jan. 30, 2018

(54) APPARATUS AND METHODS FOR OPTIMIZING INTRA CARDIAC FILLING PRESSURES, HEART RATE, AND CARDIAC OUTPUT

(71) Applicants: Daniel Walter Kaiser, Palo Alto, CA (US); Clayton Allen Kaiser, Nashville, TN (US)

(72) Inventors: Daniel Walter Kaiser, Palo Alto, CA (US); Clayton Allen Kaiser, Nashville, TN (US)

(73) Assignee: CARDIOFLOW TECHNOLOGIES, LLC, Nashville, TN (US)

( * ) Notice: Subject to any disclaimer, the term of this patent is extended or adjusted under 35 U.S.C. 154(b) by 167 days.

(21) Appl. No.: 14/597,190

(22) Filed: Jan. 14, 2015

(65) Prior Publication Data

US 2016/0199554 A1 Jul. 14, 2016

Related U.S. Application Data

(60) Provisional application No. 61/927,038, filed on Jan. 14, 2014.

(51) Int. Cl.
*A61M 1/10* (2006.01)
*A61N 1/362* (2006.01)
(Continued)

(52) U.S. Cl.
CPC .......... *A61M 1/1074* (2014.02); *A61M 1/122* (2014.02); *A61M 25/10* (2013.01);
(Continued)

(58) Field of Classification Search
CPC ................ A61F 2/2412; A61F 2/2475; A61B 2017/00575; A61B 2017/00592;
(Continued)

(56) References Cited

U.S. PATENT DOCUMENTS 4,467,807 A 8/1984 Bornzin
4,535,774 A 8/1985 Olson
(Continued)

OTHER PUBLICATIONS

Korean Intellectual Property Office, International Search Report and Written Opinion for corresponding International Application No. PCT/US2015/011474, dated May 14, 2015, 19 pages.

*Primary Examiner* — Christopher D Koharski
*Assistant Examiner* — Natasha Patel
(74) *Attorney, Agent, or Firm* — William A. English; Vista IP Law Group LLP

(57) ABSTRACT

Apparatus, systems, and methods are provided for optimizing intracardiac filling pressures and cardiac output in patients with heart failure, conduction disease, and atrial fibrillation. The system is able to adjust and optimize intracardiac filling pressures and cardiac output by adjusting heart rate and the effective amount of total body blood volume. The device includes an adjustable member that may create a mean pressure differential in order to manifest an effective "mechanical diuresis" by sequestering extraneous blood volume to the high-capacitance of the venous vasculature. The system is therefore designed to reduce intracardiac filling pressures while maintaining or even increasing cardiac output.

23 Claims, 10 Drawing Sheets

(51) Int. Cl.
*A61N 1/365* (2006.01)
*A61M 1/12* (2006.01)
*A61M 25/10* (2013.01)

(52) U.S. Cl.
CPC ....... *A61N 1/3627* (2013.01); *A61N 1/36521* (2013.01); *A61N 1/36564* (2013.01)

(58) Field of Classification Search
CPC . A61B 2017/00606; A61B 5/02; A61B 5/021; A61N 1/3627
See application file for complete search history.

(56) References Cited

U.S. PATENT DOCUMENTS 5,447,524 A 9/1995 Alt
5,676,162 A * 10/1997 Larson, Jr. ............ A61M 1/101 128/899
8,043,360 B2 10/2011 McNamara et al.
8,406,879 B2 3/2013 Shuros et al.
2002/0072680 A1* 6/2002 Schock ................ A61B 5/0215 600/486
2004/0034272 A1* 2/2004 Diaz .................. A61M 1/1037 600/18
2004/0111006 A1 6/2004 Alferness et al.
2004/0254483 A1* 12/2004 Zdeblick ........... A61B 5/02028 600/486
2005/0049692 A1 3/2005 Numamoto et al.
2006/0064059 A1 3/2006 Gelfand et al.
2006/0206029 A1 9/2006 Yair
2008/0195167 A1 8/2008 Ryan
2010/0056999 A1 3/2010 Herrera Cedeno
2010/0057192 A1 3/2010 Celermajer
2010/0222635 A1* 9/2010 Poirier ................ A61M 1/1086 600/16
2011/0190874 A1 8/2011 Celermajer
2012/0165928 A1 6/2012 Nitzan
2013/0245665 A1* 9/2013 Scandurra ............. A61M 29/02 606/194

* cited by examiner

HEMODYNAMIC DATA

| | Baseline Pressures | Pressure Differential (we created a pressure differential of ~3mmHg) |
|---|---|---|
| Inferior Vena Cava Pressure (below the pressure gradient device) | 10 | 11 |
| Right Atrial Pressure | 10 | 8 |
| PA Pressures | 49/24 | 42/21 |
| Left Atrial Pressure | 22 | 19 |
| Cardiac Output (flow) | 3.8 | 4.2 |

FIG. 4

The intracardiac electrograms (top row) and the left atrial pressure (LAP) recordings (bottom row) in a patient enrolled in the LAPTOP-HF trial, with biventricular pacing on (Fig 5A) and off (Fig 5B).

APPARATUS AND METHODS FOR OPTIMIZING INTRA CARDIAC FILLING PRESSURES, HEART RATE, AND CARDIAC OUTPUT

RELATED APPLICATION DATA

The present application claims benefit of provisional application Ser. No. 61/927,038, filed Jan. 14, 2014, the entire disclosure of which is expressly incorporated by reference herein.

FIELD OF THE INVENTION

The present invention relates to apparatus, systems, and methods for prevention and/or remediation of heart disease, e.g., for optimizing intra-cardiac filling pressures, heart rate, and/or cardiac output for patients, such as patients suffering from conduction disease, atrial fibrillation, and/or congestive heart failure.

BACKGROUND

Placing a permanent pacemaker is often the only effective treatment for patients with sick sinus syndrome, atrioventricular conduction disorders, and chronotropic incompetence (where the heart rate does not increase in proportion to the demands of the body). In these circumstances, patients may receive dual chamber pacemakers, e.g., with one pacing lead typically placed in the right atrium (RA) and a second endocardial pacing lead typically placed in the right ventricular (RV) apex. However, RV pacing is associated with increased rate of death or hospitalization from congestive heart failure. The pathophysiology for this is unclear, but growing evidence suggests that an associated increase in intra-cardiac filling pressures is the primary driver of poor outcomes. RV pacing may cause bi-ventricular dyssynchrony, which, in attempts to maintain adequate cardiac output, may result in a new equilibrium of higher intra-cardiac filling pressures, particularly left-sided filling pressures. Higher intra-cardiac pressures result in symptoms of shortness of breath, an increase in the likelihood of cardiac arrhythmias, and a decrease in exercise capacity. The only current alternative in these patients is to place bi-ventricular pacing leads, whereby a third pacing lead is placed typically into the coronary sinus of the heart in order to pace both ventricles. This results in simultaneous bi-ventricular contraction, also referred to as cardiac resynchronization therapy (CRT). CRT is associated with lower left-sided filling pressures, decreased arrhythmias, decreased heart failure hospitalizations, and decreased mortality. However, approximately ten percent (10%) of patients cannot receive CRT due to heart anatomy. Therefore, an alternative device that is able to pace the heart while maintaining lower intra-cardiac filling pressures would be advantageous.

Heart failure occurs because the body perceives a decrease in cardiac output. The normal homeostasis feedback mechanisms increase total body volume in efforts to increase stroke volume in order to maintain cardiac output by the Frank-Starling mechanism. However, as cardiac performance continues to decline, the ability of the Frank-Starling mechanism is exceeded, and an increasing total body volume continues despite no improvement in stroke volume. The body continues this volume accumulation (via fluid retention), which ultimately worsens cardiac performance and leads to congestive heart failure. In this relatively common situation, a reduction in total body volume via diuretics (against the normal feedback mechanisms) may improve cardiac function and the patient's symptoms.

Heart failure costs over thirty billion dollars annually and is expected to grow by over two hundred percent (200%) over the next twenty years. Heart failure is the leading cause of hospitalization in people over the age of sixty-five and accounts for one-fifth of all elderly admission. Despite advances in monitoring and therapies, the thirty-day readmission rate for congestive heart failure has remained extremely high and relatively unchanged (slightly over 20%) over the last two decades in the United States. In heart failure patients, increasing the heart rate may increase the cardiac output and help with diuresis. However, higher heart rates are associated with higher intracardiac filling pressures, which limit patient exercise capacity. A method to increase cardiac output without increasing intracardiac pressures would be advantageous.

Heart failure results in increased fluid retention. The increased fluid causes morbidity in a variety of ways. Increased fluid in the extremities can lead to edema and tissue congestion, increased fluid in the liver can lead to cirrhosis and liver failure, and increased fluid in the gastro-intestinal track can decrease food and drug absorption, and lead to early satiety. Increased venous pressure decreases renal perfusion pressure, which can lead to renal dysfunction and more fluid retention. However, the primary patient symptom associated with admission to the hospital is related to elevated left ventricular filling pressures. Elevated left ventricular diastolic filling pressure backs up into the left atrium and the pulmonary veins. An elevation of pulmonary venous pressure can cause tachypnea, increase respiratory dead space, and worsen oxygen exchange. In addition, elevated left-sided filling pressures can cause pulmonary edema and decreased oxygen exchange which results in shortness of breath, orthopnea (shortness of breath when laying down), and hypoxia (decreased oxygen levels).

Accordingly, apparatus, systems, and methods for optimizing intra-cardiac filling pressures, heart rate, and cardiac output in order to treat patients with conduction disease, fibrillation, and congestive heart failure would be useful.

SUMMARY

The present invention s directed to an apparatus, systems, and methods for prevention and/or remediation of heart disease, e.g., for optimizing intra-cardiac pressures, heart rate, and cardiac output for patients, such as patients suffering from conduction disease, atrial fibrillation, and congestive heart failure. More particularly, the present invention is directed to implantable devices that measure hemodynamics and help optimize intra-cardiac pressures, heart rate, and/or cardiac output for patients; and systems and methods for using such devices.

The primary treatment for patients with heart failure is to give diuretic medications to reduce total body volume, with more refractory cases requiring continuous infusion of medications to improve cardiac function. Reducing total body fluid results in less congestion, improved renal function, and a paradoxical increase in cardiac output. A device that is able to induce "mechanical diuresis" where excess fluid is sequestered elsewhere in a patient's body may be able to optimize intracardiac pressures and cardiac output similarly to diuretics. We have demonstrated that by creating a pressure gradient in the inferior vena cava, we can move extraneous and congesting fluid to the high capacitance vessels below a pressure gradient device placed within or downstream of the inferior vena cava. Given the high capacitance of the venous system, a large volume of blood can be relocated, with a significant decrease in intra-cardiac pressures and with only a minimal (if any) increase in pressure below our device.

Computer modeling has revealed that differences in bi-ventricular function are likely more important than total cardiac output in terms of patient symptoms. However discordant the ventricular function may be, the cardiac output of each ventricle must be the same. Therefore, with predominant left heart failure (or a hyperactive right ventricle), pressure builds behind the left ventricle. In predominant right heart failure (or a hyperactive left ventricle), pressure builds behind the right ventricle. Of importance, exercise/exertion exaggerates differences in ventricular function. Over time and accelerated by disease, most left ventricles develop some degree of diastolic dysfunction. Accordingly, during exercise, the left ventricle cannot “keep up with” the right ventricle. The resulting equilibrium reveals rapid elevations in left-sided filling pressures during exercise that limit exercise capacity. An interactive device that can rapidly sequester extra blood volume can limit the rise in intra-cardiac filling pressures while maintaining cardiac output would dramatically improve exercise capacity and improve patient symptoms of fatigue and shortness of breath.

Long standing elevated left atrial (LA) pressure can dilate the left atrium and contribute to atrial arrhythmias such as atrial fibrillation. It is likely that increases in ventricular pressures (both right and left ventricular pressures) may result in ventricular arrhythmias as well. By maintaining lower intracardiac filling pressures, a system that maintains cardiac output while preventing elevated intracardiac pressures may decrease deadly cardiac arrhythmias.

Cardiac output and heart rate have a complicated relationship. In patients without volume overload, increasing heart rate does not affect cardiac output. This apparent paradox occurs due to a decrease in ventricular filling time and a redistribution of blood from the heart to peripheral tissue. When venous return to the heart is not increased, the stroke volume will fall with increasing heart rate implying an extrathoracic venous collapse. However, in patients that are volume overloaded, increasing the heart rate can maintain stroke volume and increase cardiac output dramatically. The amount of improvement in cardiac output typically depends on the ability of the left ventricle to relax fast enough at higher heart rates. Therefore, optimizing cardiac output is a complex interaction between volume status, heart rate, bi-ventricular pressure-volume curves and filling parameters. Improving heart rate may increase left-sided filling pressures and exacerbate patient symptoms. Left-sided filling pressures may rise significantly with only marginal improvement in cardiac output. Therefore, the relationships between cardiac output in response to changes in left-sided filling pressures are an important consideration to optimize filling pressures and cardiac output.

In most individuals, cardiac output does not need to be increased. However, in patients with heart failure, the body senses a reduction in cardiac output. In these patients, increasing cardiac output can improve renal perfusion and urine output, thereby improving volume status. In order to most effectively titrate heart rate, the systems and methods herein may monitor both intracardiac pressures and cardiac output.

Most pacemaker systems adjust heart rate based on physiologic need (such as monitoring respiratory rate and/or patient activity) as opposed to adjusting heart rate based on intracardiac pressures, cardiac output, and total body blood volume. In most patients with volume overload, increasing the heart rate will increase the cardiac output. However, this often results in elevated left-sided filling pressures and worsening symptoms of heart failure. Therefore, while pacing improves cardiac output and volume status, it may make symptoms of heart failure worse. If the intra-cardiac pressures can be monitored and optimized with increasing heart rates, total body volume can be improved without exacerbating heart failure symptoms. Furthermore, by adjusting both heart rate and intra-cardiac filling pressures, cardiac output can be optimized. This encompasses a novel concept—to adjust cardiac output based on a measure of patient volume status in order to improve symptoms and encourage diuresis, as needed. Therefore, if a patient begins to gain excess blood volume, the systems and methods herein may increase cardiac output in efforts to diurese the excess blood physiologically.

Prior systems attempting to optimize left-sided filling pressures suggest placing a pressure sensor directly into the left atrium or left ventricle. However, such sensors are at risk of thrombus development, which may lead to thromboembolic events. By not interfering with the systemic circulation or integrity of natural barriers (such as the interatrial septum), thrombus development at the location of pressure sensors are prevented from causing systemic thromboembolic events by utilizing the ability of the lung vasculature to sequester these thrombi from reaching the brain and other key organs. Furthermore, placing a pressure sensor directly into the coronary sinus, with or without an occlusion, the pressure of the left ventricle may be estimated.

Additionally, monitoring changes in right ventricular or pulmonary pressures—or combining right ventricular or pulmonary pressures with an estimate of stroke volume—may be used to estimate left-sided filling pressures without requiring a sensor in the left atrium. Mild changes in the pressure gradient in the inferior vena cava, for example, may cause slight changes in right-sided filling pressures and subsequent changes in stroke volume by the Frank-Starling mechanism. However, if the left ventricle is unable to increase the stroke volume similarly, the pressure of the left ventricle, left atrium, pulmonary artery, and right ventricle increase. This increase in afterload decreases right ventricular stroke volume until it equals the stroke volume of the left ventricle. Therefore, when mild changes in the pressure gradient mechanism causes a significant increase in right or left sided pressures, this suggests the additional volume did not improve cardiac output. Therefore, only changes in pressure (or changes in stroke volume) are necessary to estimate the pressure differential required to maximize cardiac output.

In accordance with an exemplary embodiment, the apparatus, systems, and methods herein may determine an elevation in total body blood volume and optimize cardiac output by adjusting heart rate in efforts to improve volume status through increased renal perfusion and therefore increased diuresis. In addition, the apparatus and systems herein may control the intra-cardiac filling pressures by creating a pressure differential in a vessel such as the inferior vena cava. The pressure differential may sequester extraneous blood volume to the high-capacitance of the venous system. The apparatus and systems herein may manifest an effective “mechanical diuresis” to improve myocardial hemodynamics. Optionally, the apparatus, systems, and methods herein may also pace the right ventricle in patients requiring pacing, and/or simultaneously may prevent the rise in intra-cardiac pressures associated with right ventricular pacing to improve the symptoms and outcomes of patients. Therefore, the apparatus and systems herein may be an alternative to placing a pacing lead in the coronary sinus (bi-ventricular pacing), which is the primary treatment option for most patients requiring right ventricular pacing and may be the only treatment option for up to ten percent (10%) of patients that have inadequate coronary anatomy for the additional pacing lead.

Optionally, the systems and methods herein may also communicate to the patient their total body blood volume status and/or help manage their medical management. In addition or alternatively, the apparatus, systems, and methods may be responsive to patient activity to optimize cardiac performance and intracardiac pressures to improve exercise capacity. Furthermore, decreasing intra-cardiac pressures may reduce ectopic beats, thereby reducing dangerous and symptomatic arrhythmias. In addition, reducing intracardiac pressures may result in remodeling that improves myocardial function and hemodynamics. Thus, the apparatus, systems, and methods herein may therefore improve patient respiratory symptoms, improve cardiac output and/or encourage diuresis to reduce total body volume, improve exercise capacity, guide patient medication dosing, prevent atrial and ventricular arrhythmias, prevent negative heart failure remodeling, decrease heart failure hospitalization rates, and/or improve the quality and duration of life.

In accordance with another embodiment, the apparatus, systems, and methods herein may include implantation of a device that monitors pressures in and around the heart, as well as the cardiac output, and accordingly adjusts heart rate and a pressure gradient, such as through the inferior vena cava. The pressure gradient and heart rate may be adjusted to optimize the filling pressures inside of the heart and the cardiac output. In response to measurements of cardiac output and/or sensors of pressure measurements, at least one pressure gradient and/or the heart rate are adjusted to optimize hemodynamics.

Monitoring intracardiac filling pressure may include one or more pressure sensors located in the coronary sinus, pulmonary circulation, right ventricle, right atrium, left atrium, and/or vena cava. In addition or alternatively, monitoring stroke volume or cardiac output may be determined by assessing for changes in electrical impedance or changes in oxygen saturation, such as, determined by light oximetry.

In accordance with still another embodiment, systems and methods may be provided for determining optimal estimated left sided filling pressure within a patient's heart. The system and methods may gradually adjust the pressure differential and/or heart rate in order to create pressure-cardiac output relationships. The systems and methods may periodically be gradually adjusted to alter the pressure differential, which may result in a new estimated left sided filling pressure and a measured cardiac output, which may be recorded. Optionally, the heart rate may also periodically be gradually adjusted, which may result in a new estimated left sided filling pressure and measured cardiac output which can be recorded. Therefore, by altering the pressure differential and heart rate, the systems and methods may maximize cardiac output with respect to intracardiac filling pressures. Pressure-cardiac output relationships may be determined in order to identify the optimal pressure differential and heart rate in order to optimize cardiac output at an acceptable rise in the estimated left sided filling pressures at various patient activity levels.

In another embodiment, systems and methods may be provided to create a pressure differential that include one or more shunts, balloons, orifices, valves, constriction mechanism, and the like, e.g., to increase a pressure drop through the tricuspid valve, superior vena cava, inferior vena cava, pulmonary artery, and/or right atrium.

In accordance with an exemplary embodiment, a system is provided for implantation in the body of a patient with conduction disease and/or heart failure configured to monitor and/or treat the patient. The system may include at least one sensor configured to provide sensor data corresponding to pressures within or near the heart; at least one adjustable component configured to create a pressure gradient to blood flow; at least one pacing component configured to at least one of sense and pace the heart; and a controller configured for adjusting the function of at least one component based at least in part on sensor data from at least one sensor.

Optionally, the system may include at least one additional sensor configured to provide sensor data corresponding to the stroke volume or cardiac output. In one embodiment, the at least one additional sensor comprises a plurality of electrodes configured to measure changes in electrical impedance that correlate with changes in blood volume. The controller may be coupled to the plurality of electrodes and configured to estimate cardiac output by measuring the changes in electrical impedance from the plurality of electrodes. For example, at least one catheter, lead, or other elongate member may have two or more electrodes along the catheter capable of measuring electrical impedance. In another embodiment, the at least one additional sensor may be a flow sensor capable of measuring the blood oxygen saturation, such as with a light oximeter. The controller may be configured to estimate left-sided filling pressures by analyzing sensor data from at least two of these sensors.

In still another embodiment, the at least one pressure sensor may be configured to be located in the pulmonary artery, right atrium, superior vena cava, inferior vena cava, right ventricle, left atrium, and/or coronary sinus (or any vein of the heart), e.g., carried by a lead implanted in the patient's body.

In an exemplary embodiment, the at least one adjustable component may be configured to be placed percutaneously and selectively expanded in the vena cava with a mechanism to induce a pressure gradient along the inside of the adjustable component. In one embodiment, the adjustable component may be an expandable member, e.g., an inflatable balloon or a self-expanding mechanism. In another embodiment, the adjustable component may be a tubular member that may be selectively actuated to change shape and/or size. In yet another embodiment, the adjustable component may be connected to an electrical motor that may induce changes to the adjustable component.

In any of these embodiments, the controller may utilize changes in blood pressure to induce a mechanical change in the adjustable component. For example, filling pressures of the right atrium may fluctuate, e.g., from about 5 mmHg to about 10 mmHg, while the pressure below or upstream of the adjustable device may maintain a pressure of about 10 mmhg. The controller may actuate the flow impedance device to use energy from this higher pressure to create a pressure drop across the device, e.g., to use the pressure differential that occurs during the normal heart cycle to create a pressure gradient.

In yet other embodiments, the adjustable component may create a pressure gradient by at least one of the following: i. adjusting blood flow impedance across the tricuspid valve; ii. decreasing the size of the right ventricle; iii. adjusting blood flow impedance through the superior vena cava; iv. adjusting blood flow impedance through the inferior vena cava; v. adjusting blood flow impedance through the azigous vein; vi. adjusting blood flow impedance through the right ventricle or tributary; vii. adjusting blood flow impedance through the pulmonary valve and/or pulmonary artery; and viii. adjusting blood flow impedance from the left atrium into a lower pressure conduit.

In addition or alternatively, the blood flow impedance may be adjusted by at least one of: i. inflating a balloon; ii. where the adjustable component has a certain shape, including but not limited to, a doughnut shaped structure where blood flows through the structure; iii. changing the size or orientation of a shunt; iv. shunting the direction of blood flow; v. adjusting the size of a conduit; vi. a rotating propeller; vii. adjusting the cross-sectional area of blood flow; and viii. adjusting a valve, where the valve includes one of a ball valve, shutter valve, butterfly valve, diaphragm valve, gate valve, globe valve, knife valve, spool valve, thermal expansion valve, and a pressure reducing valve.

In exemplary embodiments, the adjustable component may be located in the patient's inferior vena cava or below the renal veins. Alternatively, the adjustable component may be located outside a blood vessel in the patient's body.

Optionally, in any of these embodiments, the system may include at least one sensor configured to correlate with patient activity, such as with an accelerometer device.

In accordance with another embodiment, during operation of the system, the controller may change the function of at least one component in order to assess and/or record changes from at least one sensor component. For example, the controller may determine the function of at least one component based on changes in sensor data in response to changes in function of at least one component.

In addition or alternatively, the controller may maintain a minimum acceptable cardiac output and a maximally allowable left-sided filling pressure. For example, the minimum acceptable cardiac output and the maximally allowable left-sided filling pressure may be influenced by sensor data.

In addition or alternatively, the controller may be configured for adjusting the function of at least one component based at least in part on prior recordings from the system and current recordings from at least one sensor.

Optionally, in any of these embodiments, sensor data and/or device functioning details may be transmitted outside of the patient, e.g., using a transmitter or transceiver carried by the controller or other component of the system. In addition or alternatively, the functionality of the device may be adjusted from outside of the patient's body, e.g., by communicating with the system using a receiver or transceiver carried by the controller or other component of the system.

In another option, in any of these embodiments, the system may also include one or more pacing electrodes, and the controller may be configured to adjust the pacing parameters of the one or more pacing electrodes in response to sensor data.

In still another embodiment, the adjustable component may be at least partially fabricated from animal tissue (such as bovine or porcine tissue), Nitinol, synthetic fluoropolymer, stainless steel, chromium compounds, and/or various polyesters.

In accordance with another exemplary embodiment, a system is provided for implantation in the body of a patient with conduction disease and/or heart failure configured to monitor and/or treat the patient that includes a catheter, lead, or other elongate member sized for implantation within a patient's body, e.g., such that at least one end of the lead is positioned within a chamber of the patient's heart, a blood vessel, and/or other body lumen. The system may include at least one sensor carried by the elongate member and configured to provide sensor data corresponding to pressures within or near the heart. The system also includes at least one adjustable component configured to create a pressure gradient to blood flow carried by the elongate member or a second catheter, lead, or elongate member. The system also includes at least one pacing component configured to at least one of sense and pace the heart, and a controller configured for adjusting the function of at least one component based at least in part on sensor data from at least one sensor.

In one embodiment, the elongate member includes a proximal end coupled to a housing containing the controller and a distal end sized for introduction into the patient's heart, and wherein the at least one pressure sensor and the at least one component are carried by the elongate member. For example, the elongate member may include a first branch on the distal end carrying the at least one pressure sensor, and a second branch on the distal end carrying the at least one component. In an exemplary embodiment, the elongate member is a catheter including an inflation lumen extending between the proximal end and the second branch, and wherein the at least one component includes a balloon comprising an interior communicating with the inflation lumen for delivering and removing inflation media into and from the interior.

In another exemplary embodiment, the elongate member is a catheter including first and second inflations lumen extending between the proximal end and the second branch, and wherein the at least one component comprises a first balloon comprising a first interior communicating with the first inflation lumen and a second balloon comprising a second interior communicating with the second inflation lumen such that inflation may be delivered into and removed from the first and second interiors to independently expand and collapse the first and second balloons.

Optionally, the system may include an actuator member extending from the elongate member proximal end to the second branch, and wherein the at least one component comprises a mechanically expandable member coupled to the actuator member for selectively expanding and collapsing the expandable member.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It will be appreciated that the exemplary apparatus shown in the drawings are not necessarily drawn to scale, with emphasis instead being placed on illustrating the various aspects and features of the illustrated embodiments.

FIG. 4 is a table showing exemplary hemodynamic data obtained by creating a pressure differential in the inferior vena cava.

DETAILED DESCRIPTION OF THE EXEMPLARY EMBODIMENTS

Figure 1:
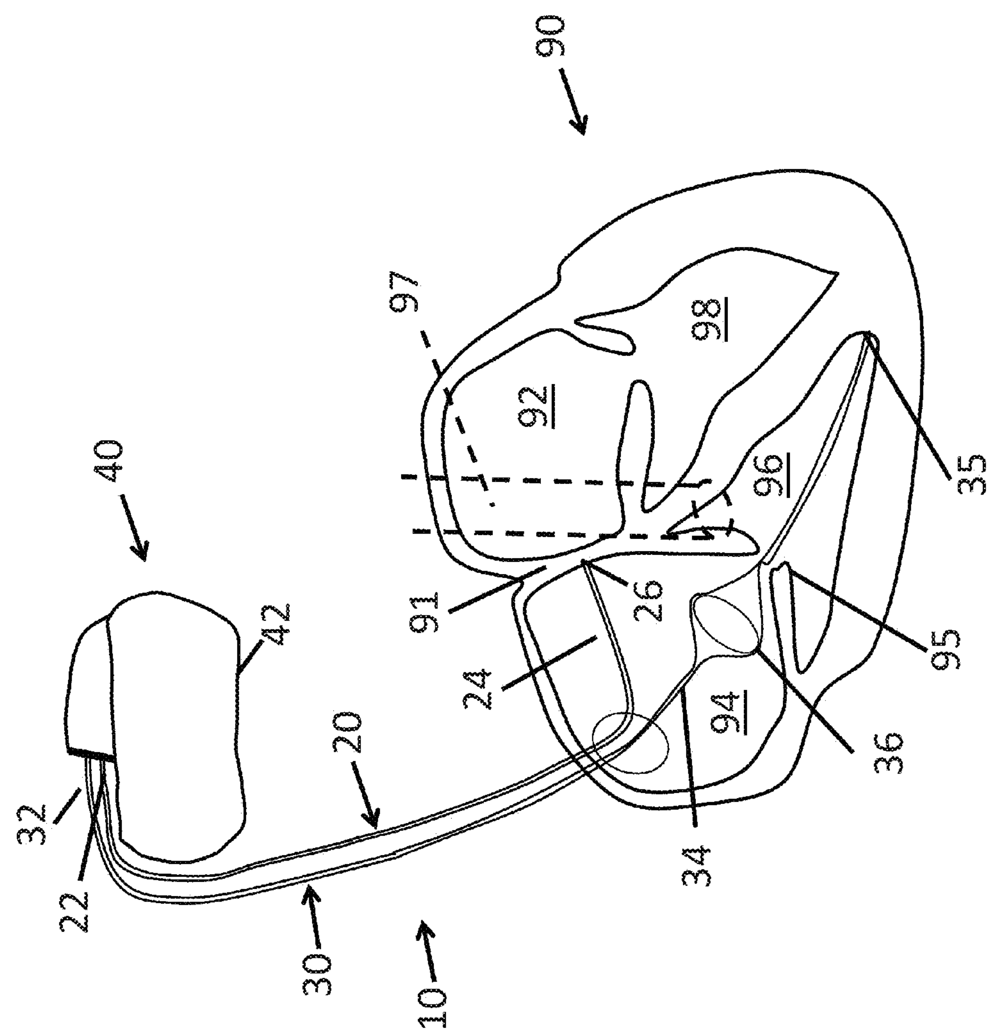
FIG. 1 shows an exemplary embodiment of a system implanted within a patient's body.

Turning to the drawings, FIG. 1 shows an exemplary embodiment of a system 10 that may be implanted within a patient's heart 90 for prevention and/or remediation of heart disease, e.g., for optimizing intra-cardiac filling pressures, heart rate, and/or cardiac output for patients, such as patients suffering from conduction disease, atrial fibrillation, and/or congestive heart failure. In the embodiment shown, the system 10 includes first and second leads 20, 30 coupled a controller 40 for operating the system 10, e.g., to perform the various methods and/or functions described elsewhere herein.

As shown, the first lead 20 includes a first or proximal end 22 coupled to the controller housing 42 and a second or distal end 24 sized for introduction into the patient's heart 90, e.g., into the right atrium 94. The distal end 24 may include one or more features, e.g., a screw tip or other anchor (not shown), for securing the distal end 24 relative to the heart 90, e.g., into the septum 91 between the right atrium 94 and the left atrium 92. In addition, one or more sensors 26 (one shown) may be provided on the distal end 24 that may be coupled to the septum 91, e.g., to provide signals corresponding to the pressure within the left atrium 92. One or more wires or other conductors (not shown) may extend between the proximal and distal ends 22, 24 to communicate the signals from the sensor(s) 26 to the controller 40.

Similarly, the second lead 30 may include a proximal or first end 32 coupled to the housing 42 and a distal or second end 34 sized for introduction into the patient's heart 90, e.g., into the right atrium 94, through the tricuspid valve 95 into the right ventricle 96. The second lead 30 includes an expandable member 36 on the distal end 34, e.g., offset proximally by a predetermined distance from a distal tip 35 of the second lead 30 such that the expandable member 36 is located within the right atrium 94 and/or the tricuspid valve 95. As described further below, the expandable member 36 may be sized to expand and at least partially fill a chamber or other body lumen within the patient's body, e.g., within the right atrium 94. Optionally, similar to the first lead 20, the second lead 30 may include one or more features, e.g., a screw tip or other anchor (not shown), on the distal tip 35 to secure the distal end 34 within and/or relative to the patient's heart 90, e.g., the wall of the heart 90 within the right ventricle 96, similar to pacing leads.

Alternatively, the first and second leads may be provided on a single device with a branched distal end (not shown), e.g., with the one or more sensors on a first branch and the expandable member on a second branch of the lead, as described elsewhere herein.

In one embodiment, the expandable member 36 may be a compliant balloon configured to expand between a collapsed configuration and one or more expanded configurations, e.g., that at least partially fill the right atrium 94 (or other body lumen) and/or occlude flow into or through a body lumen within or adjacent the heart 90, as described further elsewhere herein. For example, the expandable member 36 may be a balloon formed from an elastic material such that the balloon 36 may be inflated to a variety of different expanded sizes, e.g., to change the volume the balloon 36 occupies within the right atrium 94 and/or enhance sealing engagement between the balloon 36 and surrounding tissue. Alternatively, the expandable member 36 may be a non-compliant balloon formed from substantially inelastic material such that the balloon 36 expands to an expanded configuration having a pre-configured shape and/or size.

In this embodiment, the second lead 30 may be a catheter including an inflation lumen (not shown) extending between the proximal end 32 and the distal end 34 and communicating with an interior of the balloon 36. The controller 40 may include a pump or other source of inflation media (not shown) therein, which may be delivered into and/or removed from the balloon 36 via the inflation lumen, e.g., to direct the balloon 36 between the collapsed configuration and the one or more expanded configurations.

Alternatively, the expandable member 36 may be a mechanically expandable device, which may expand and/or otherwise change shape in response to the controller 40. For example, one or more cables or other actuator members (not shown) may extend between the proximal and distal ends 32, 34 of the second lead 30, e.g., coupled to an actuator (not shown) within the housing 42 and an expandable frame (e.g., covered by a membrane, not shown) or other structure of the expandable member 36. In this manner, the controller 40 may actuate the expandable member 36 to expand and collapse the expandable member 36 between one or more different sizes and/or shapes.

Optionally, the controller 40 may be part of a pacing system, which may include one or more pacing electrodes (not shown) on one or both of the leads 20, 30, and/or other leads (not shown) implanted within the patient's heart 90. Examples of such systems and components that may be incorporated into the systems described herein are disclosed in U.S. Pat. Nos. 4,467,807, 4,535,774, 5,447,524, 8,043,360, and 8,406,879, and U.S. Publication Nos. 2003/7159593, 2004/0111006, 2005/0049692, 2006/0206029, 2010/0056999, 2010/0057192, 2011/0190874, and 2012/0165928, the entire disclosures of which are expressly incorporated by reference herein. For example, a plurality of electrodes (not shown) may be provided on the first and/or second leads 20, 30, as desired, e.g., within the right atrium 94, the right ventricle 96, and/or elsewhere to provide pacing signals to the heart 90. In an exemplary mode of operation, the controller 40 may acquire signals from the pressure sensor(s) 26. In one embodiment, the sensor(s) 26 may acquire electrical or other signals via the septum 91 that correspond to pressure within the left atrium 92 or left ventricle 98. Alternatively, a pressure sensor on the distal end 24 may be directed through the septum 91 into the left atrium 92 (not shown) to acquire pressure data directly.

Based at least partially on the signals acquired by the sensor(s) 26, the controller 40 may expand the expandable member 36 to one or more desired sizes. For example, if the expandable member 36 is a balloon positioned within the right atrium 94, the controller 40 may gradually increase and/or otherwise modify the size of the balloon 36 to at least partially fill the right atrium 94. As the balloon 36 fills the right atrium 94, the volume may be adjusted to reduce or otherwise provided a desired pressure gradient across the expandable member 32. Alternatively, the balloon 36 may be expanded within the tricuspid valve 95 to induce a pressure gradient across the valve 95, i.e., from the right atrium 94 into the right ventricle 96.

The resulting pressure gradient resulting from the expandable member 36 may cause blood volume to translocate from the pulmonary artery 97, lung circulation (not shown), left atrium 92, and/or left ventricle 98 to the venous system behind the expandable member 36. In this manner, the controller 40 may adjust the size and/or configuration of the expandable member 36 over time, e.g., based upon cardiac output trends and/or pressure measurements within the left atrium 92 or left ventricle 94 and, optionally based on activity level or other aspects of the patient's condition. However, such adjustments may be independent of heart beat, i.e., the expandable member 36 may not expand and collapse in synchronization with beating of the heart 90, but instead may be maintained at a desired size, which then be adjusted slowly over time based on pressure changes. For example, the controller 40 substantially continuously or periodically or otherwise intermittently acquire pressure data and adjust the size of the expandable member 36 at a rate substantially slower than the patient's heart rate, e.g., over multiple heart beats, seconds, or minutes.

Furthermore, in patients with volume overload, providing more pre-load to the right ventricle 96 may cause an increase in right ventricular afterload with no change in cardiac output. This may result because the left ventricle 98 is on the "flat" part of the Frank-Starling curve. Providing more pre-load to the right ventricle 96 therefore results in higher intracardiac filling pressures but no change in cardiac output. Unlike conventional treatments, when the expandable member 36 decreases the pressure gradient and thereby increases the filling pressure to the right ventricle 96 without a change in cardiac output (for example by measuring electrical impedance change from electrodes 82), these measurements may be used to identify the heart 90 is not benefiting from additional filling pressure. In addition, the system 10 may monitor changes in pulmonary or left-sided filling pressures in response to small changes in right ventricular filling pressures, thereby again identifying when the heart 90 is not benefiting from the additional filling pressure without measuring changes in cardiac output. In these circumstances, the controller 40 may be programmed to change the expandable member 36 to re-increase the pressure gradient, e.g., in order to collect more extraneous blood volume to the high capacitance venous system below the expandable member 36. In these examples and others, the system 10 may identify the optimal filling pressure and/or heart rate in order to optimize the cardiac output without causing significant elevations in left-sided filling pressures.

Optionally, the controller 40 may include one or more communication devices, e.g., a transmitter and/or receiver, for communicating with external devices (not shown). For example, the controller 40 may transmit one or more of pressure, heart rate, and cardiac output data to an external recording device, which may be used to monitor the patient over time. In addition or alternatively, the controller 40 may be sent instructions from an external device, e.g., to change parameters related to operation of the expandable member 36, pacing parameters, and the like.

Figure 2:
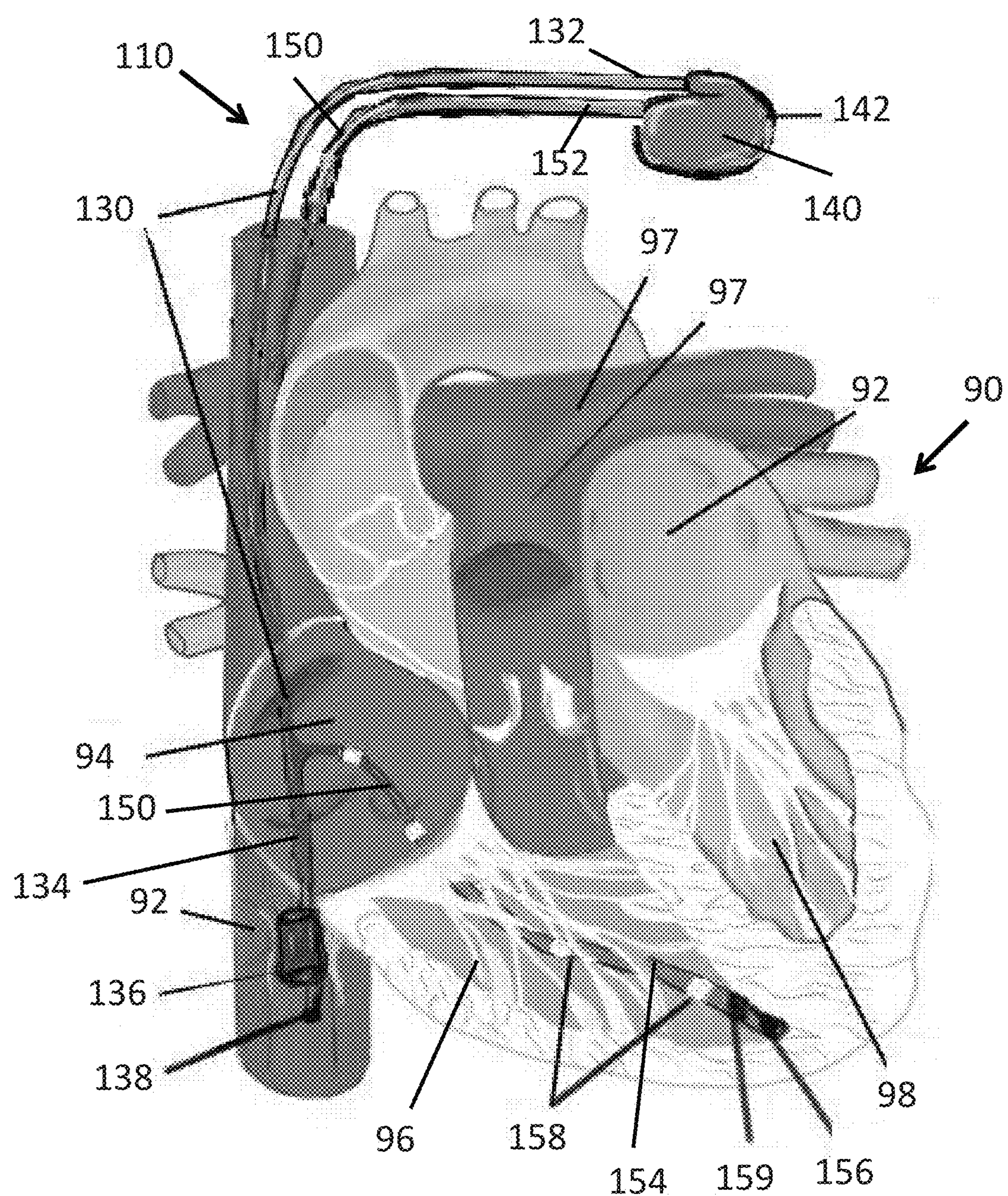
FIG. 2 shows another exemplary embodiment of a system implanted within a patient's body.

Turning to FIG. 2, another exemplary embodiment of a system 110 is shown that may be implanted within a patient's body, e.g., to determine the heart rate and/or the pressure gradient based at least in part on the measured pressures or impedance measurements. Generally, the system 110 includes one or more leads, e.g., a first or flow impedance lead 130 and a second or pacing/sensing lead 150, and a controller 140, similar to other embodiments herein.

The controller 140 generally includes one or more processors, memory, and/or other components (not shown) sealed within a housing 142, which may be sized to be implanted within the patient's body, e.g., outside but adjacent to the heart 90. The housing 142 may include one or more additional components for operating the system 110, such as a battery or other power source, one or more transmitters and/or receivers, and the like (all not shown). Optionally, an accelerometer may be provided, e.g., also within the housing 142 and coupled to the controller 140 to measure changes in patient movement, which may be used to estimate patient activity.

The controller 140 is generally coupled to the leads 130, 150 to receive sensory data from the heart 90 and/or deliver therapy to the patient. In one embodiment, the second lead 150 includes a proximal end 152 coupled to the housing 142 and a distal end 154 sized for introduction into the patient's heart 90, e.g., into the right ventricle 96. The second lead 150 includes one or more right ventricular pacing electrodes 156 (one shown) on the distal end 154, which may be coupled to controller 140, e.g., to measure heart electrical activity and/or to pace the right ventricle 96. In addition, the second lead includes a plurality of sensors 158 coupled to the controller 140 to measure electrical impedance, e.g., between pairs of the sensors 158 and/or other pacing components of the system 10, such as the RV pacing electrode 156 and/or the right atrial pacing electrode (not shown). The controller 140 may use changes in the impedance measurements to estimate right ventricular volume, e.g., to determine stroke volume. The cardiac output of the right ventricle 96 approximates the cardiac output of the left ventricle 98, and, therefore, the total cardiac output may be estimated by measuring the impedance changes along the sensors 158. Optionally, the controller 140 may also be connected to a pacing lead (not shown), e.g., positioned within the right atrium (94) to sense and pace the heart atria.

The first lead 130 may include a proximal end 132 coupled to the housing 142 and a distal end 134 sized for introduction into a body lumen, similar to other embodiments herein. The distal end includes a flow impedance device 136 that may be controlled by the controller 40 to induce a pressure gradient to blood flow through the device 136, such as located in the inferior vena cava 92. The flow impedance device 136 may be configured to control the pressure gradient in a variety of methods, as described further elsewhere, e.g., with reference to FIG. 3. Configuration changes in the flow impedance device 136 may translocate more total body blood volume to the high capacitance located behind the flow impedance device 136.

The first lead 130 may also include a sensor 138 on the distal end 134 distally beyond the flow impedance device 136. The sensor 138 may be coupled to the controller 140 to measure the pressure of blood beyond the flow impedance device 136, e.g., upstream within the inferior vena cava 92.

Similarly, the right ventricular lead 150 may also include a sensor 159 on the distal end 154 coupled to the controller 140 and configured to measure the pressure within the right ventricle 96. In one embodiment, the sensor 159 may be configured to measure pressure waveforms within the right ventricle 96 and the controller 140 may use waveform analysis to estimate the pressure waveforms in the pulmonary artery 97. Utilizing estimates of cardiac output and pulmonary artery pressure waveforms may be used to estimate the pressure of the left atrium 92 and left ventricle 98 e.g., as described elsewhere herein.

Using the estimates of intracardiac filling pressures from the pressure recordings determined from the sensor 159 and estimates of the cardiac output from measurements along the sensors 156, the controller 140 may adjust the pressure differential from the flow impedance device 136 and/or pacing from the pacing electrode 156 with the resulting changes in cardiac output and filling pressure monitored and recorded. For example, from these measurements, the optimal pressure differential, heart rate, and/or cardiac output may be determined and implemented.

In another exemplary embodiment, when the pacing lead 150 is introduced to pace the right ventricle 96, the pacing electrode 156 may be positioned along the base, the septum, or the outflow tract of the right ventricle 96. Since the balance of ventricular function is more important than the absolute pumping function, pacing the heart 90 at different locations may worsen right ventricular stroke volume. Therefore, in circumstances where the right ventricular function exceeds the left ventricular function, pacing of the right ventricle 96 at different locations may cause irregular activation of the right ventricle 96 in order to equalize the function of each ventricle. The method may lower left-sided filling pressures.

Figure 3:
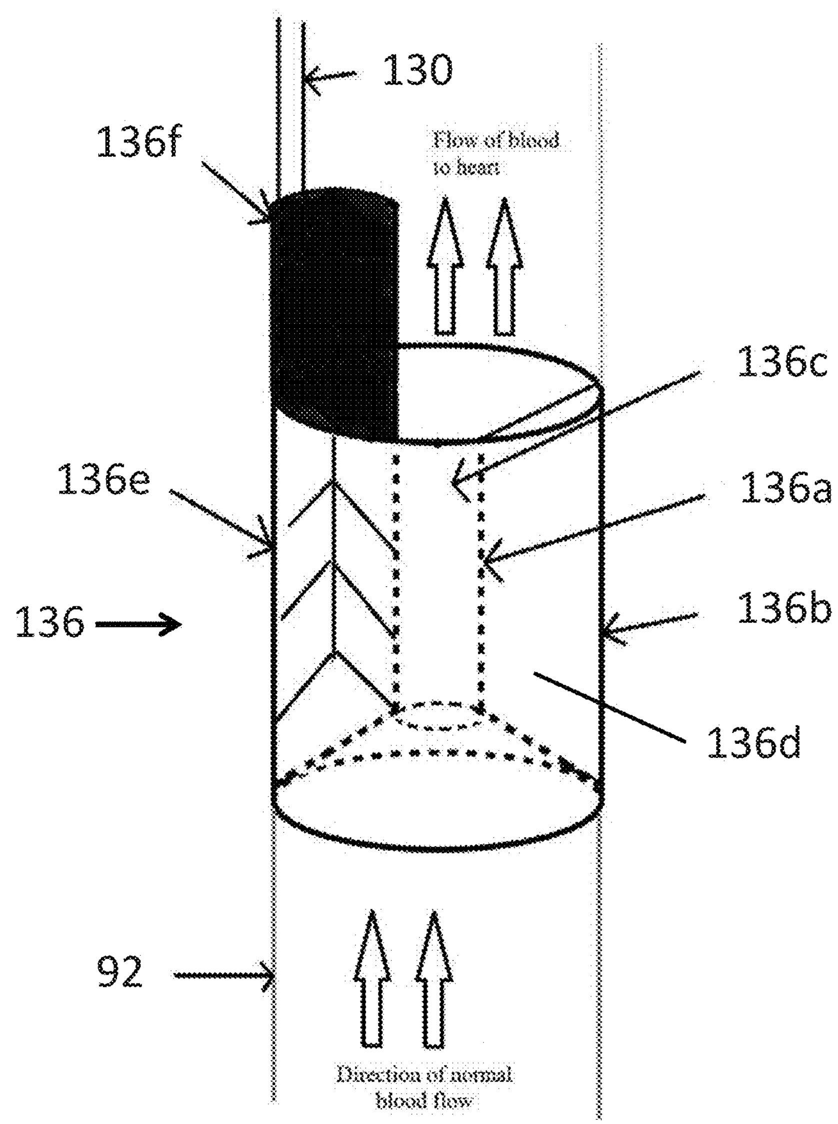
FIG. 3 shows an exemplary embodiment of a device for creating a pressure differential within a patient's body that may be included in a system such as those shown in FIGS. 1 and 2.

Turning to FIG. 3, an exemplary embodiment of a flow impedance or pressure differential device 136 is shown that may be provided on the first lead 130. As shown, the flow impedance device 136 generally includes an inner membrane **136*a* and an outer membrane 136*b*, which are sized and/or otherwise configured to be placed within the inferior vena cava 92, e.g., using a percutaneous method. The inner and outer membranes 136*a*, 136*b* may be concentrically disposed relative to one another such that the inner membrane 136*a* defines an inner flow passage 136*c* through the flow impedance device 136 and a region 136*d* is defined between the inner and outer membranes 136*a*, 136*b***, e.g., having an annular or other shape.

The flow impedance device 136 also includes a pressure control mechanism **136*e*, e.g., disposed within the region 136*d* and an electrical motor or other actuator 136*f* coupled to the pressure control mechanism 136*e*. For example, the actuator 136*f* may be coupled to the controller 140 (shown in FIG. 2) for operating the pressure control mechanism 136*d* within the flow impedance device 136, e.g., by converting electrical energy from the controller 140 to cause a mechanical change in the pressure control mechanism 136*e***.

In exemplary embodiments, the pressure control mechanism **136*e* may be configured for changing one or more of the cross sectional area to the inner flow passage 136*c*, changing the direction or length of blood flow, requiring pressure from below the flow impedance device 136 to move or change an aspect of the pressure control mechanism 136*e*, and/or changing the orientation of the pressure control mechanism 136*e*. For example, the pressure control mechanism 136*e* may include a set of struts or other structures that mechanically expand or contract to cause the inner membrane 136*a* to move inwardly or outwardly relative to the inner flow passage 136*c*, thereby constricting or opening the inner flow passage 136*c*. Using one or more of these mechanisms, the flow impedance device 136 may induce a pressure gradient such that the mean pressure across the flow impedance device 136 may be controlled. Because the capacitance of the venous system connected to the inferior vena cava 92 below or upstream of the flow impedance device 136 is much higher than the arterial system, small changes in the pressure gradient result in a large translocation of blood volume from the pulmonary and arterial system to the venous system below or upstream of the flow impedance device 136 and/or inferior vena cava 92. Thus, the operation of the flow impedance device 136** may result in an effective "mechanical diuresis."

FIG. 4 shows exemplary pressure recordings obtained during experiments in which a pressure differential was created along a device placed in the inferior vena cava 92, similar to the flow impedance device 136 shown in FIG. 3. The pressure differential imposed across the device was approximately 3 mmHg. The subsequent intracardiac filling pressures revealed a reduction in right atrial pressure, a reduction in pulmonary artery pressures, and a reduction of left atrial pressure. Thus, with the pressure differential, a higher cardiac output was created and a higher flow resulted through the flow impedance device.

Figure 5A:
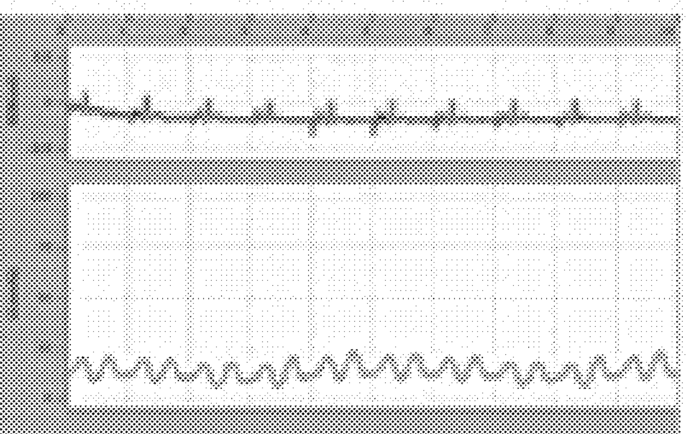
FIGS. 5A and 5B are tables showing exemplary data of the relationship between left atrial pressure and bi-ventricular pacing.
Figure 5B:
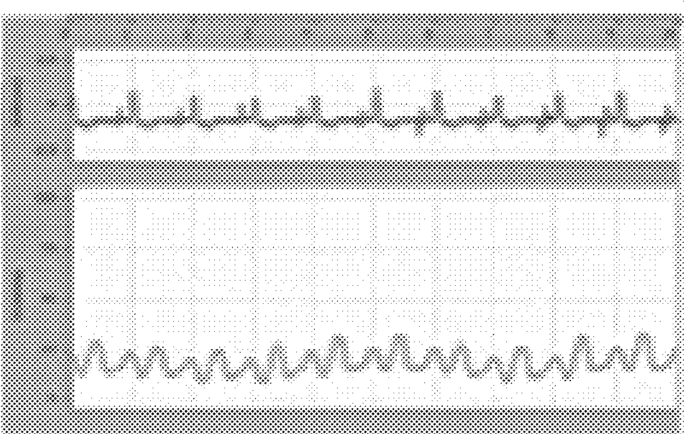

FIGS. 5A and 5B are tables showing published data relating left atrial pressure to bi-ventricular pacing. As can be seen, bi-ventricular pacing is associated with a reduction in left-sided filling pressures. This is likely the primary method by which bi-ventricular pacing improves symptoms and exercise capacity. An interactive device that can maintain intra-cardiac pressures may achieve similar benefits of bi-ventricular pacing. Therefore, patients who are not candidates for bi-ventricular pacing may benefit from an interactive device that creates a pressure differential to blood flow.

Figure 6:
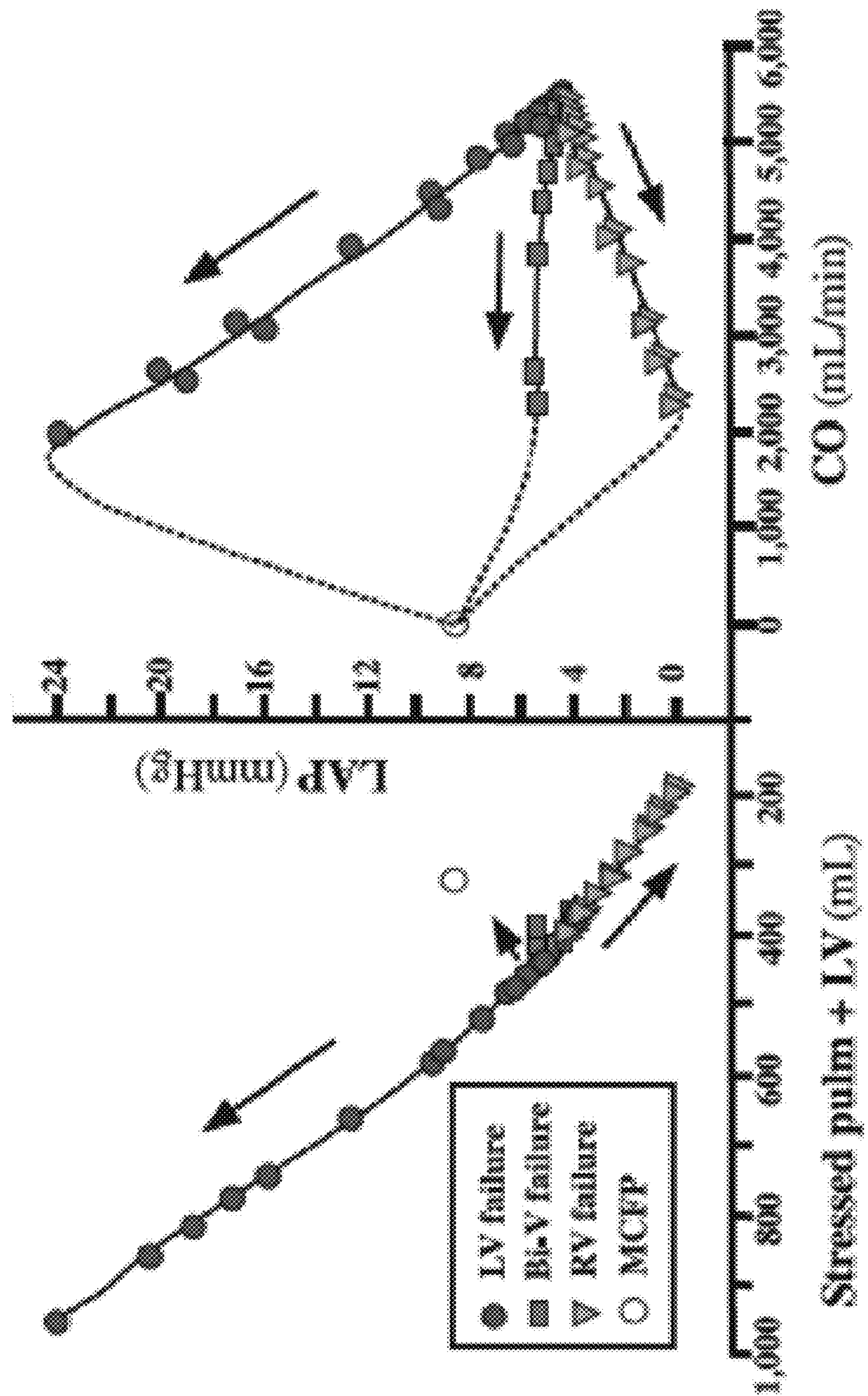
FIG. 6 is a graph showing exemplary computer modeling data relating discordant bi-ventricular function to cardiac output, left atrial pressure, and left atrial plus pulmonary circulation blood volume.

FIG. 6 is a graph showing computer modeling data relating discordant bi-ventricular function to cardiac output, left atrial pressure, and left atrial plus pulmonary circulation blood volume. As can be appreciated, the relationship between ventricular function is more important in determining intra-cardiac filling pressures compared to absolute ventricular function. Therefore, a device that monitors the function of the heart and intracardiac filling pressures may be able to alter the heart rate and intracardiac filling pressures in order to help to balance ventricular function to improve optimize cardiac output and intracardiac filling pressures.

Figure 7:
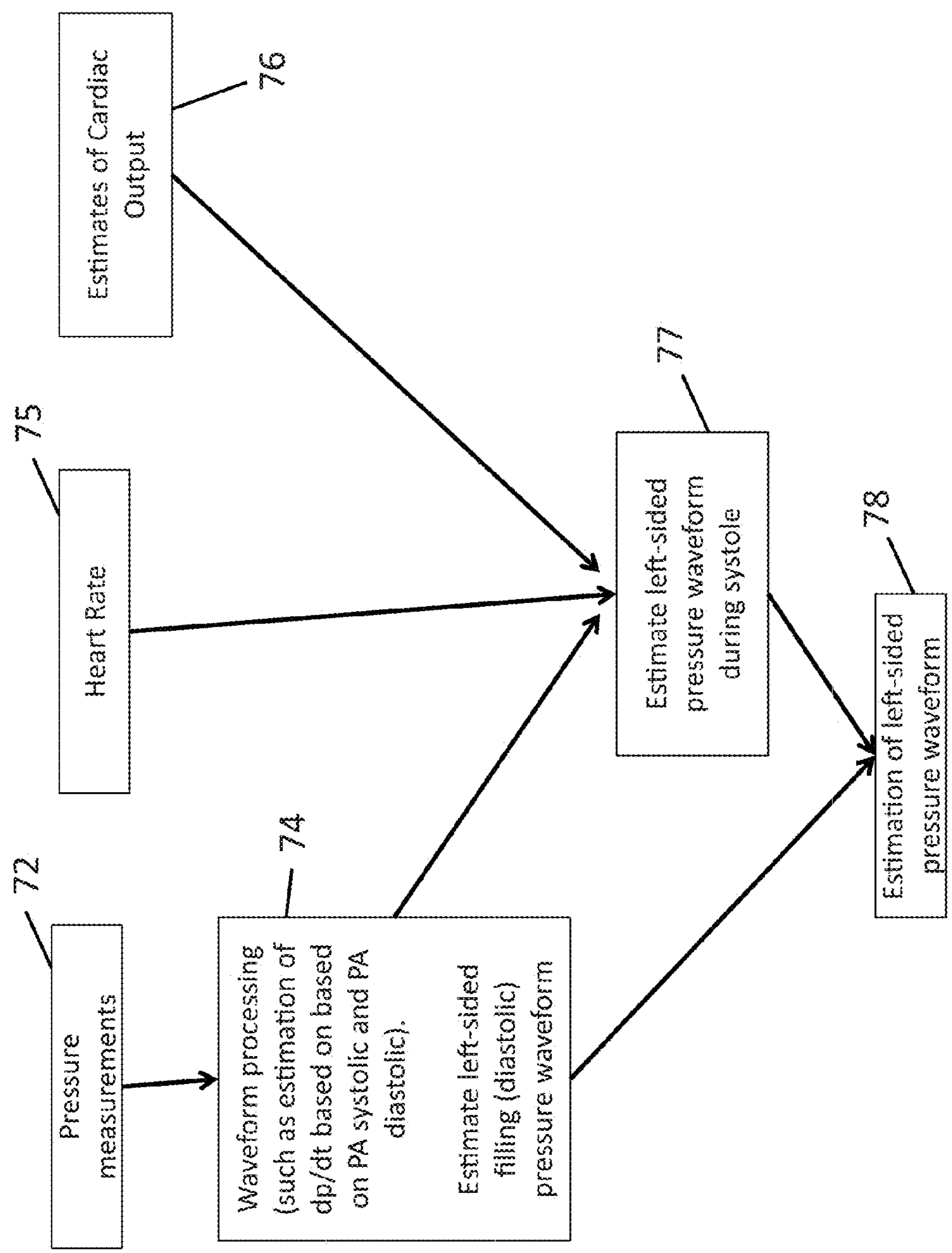
FIG. 7 is a flow chart showing an exemplary method for using pressure measurements, heart rate, and estimates of cardiac output to estimate left-sided filling pressures.

Turning to FIG. 7, an exemplary method is shown in which pressure measurements from the right ventricle, obtained at step 72, e.g., using any of the systems described herein, may be combined with cardiac output measurements in order to estimate the left-sided pressure waveform. At step 74, the pressure waveform from the right ventricle may be used to estimate the pulmonary artery (PA) diastolic pressure (which is the pressure when the right ventricular volume begins to decrease) as well as the pulmonary artery (PA) systolic pressure (which is the peak pressure measured in the right ventricle).

At steps 75 and 76, the heart rate and cardiac output (again obtained using any of the systems herein) may then be used to estimate the rate of pressure decline (dp/dt), which may be used to estimate left-sided diastolic pressure waveforms, at step 77. Furthermore, by combining systolic waveforms with estimates of stroke volume, left-sided systolic waveforms may be estimated at step 78. Therefore, the maximum left-sided filling pressures and effective left-sided filling pressures (LVEDP) may be estimated using any of the systems described herein.

Figure 8A:
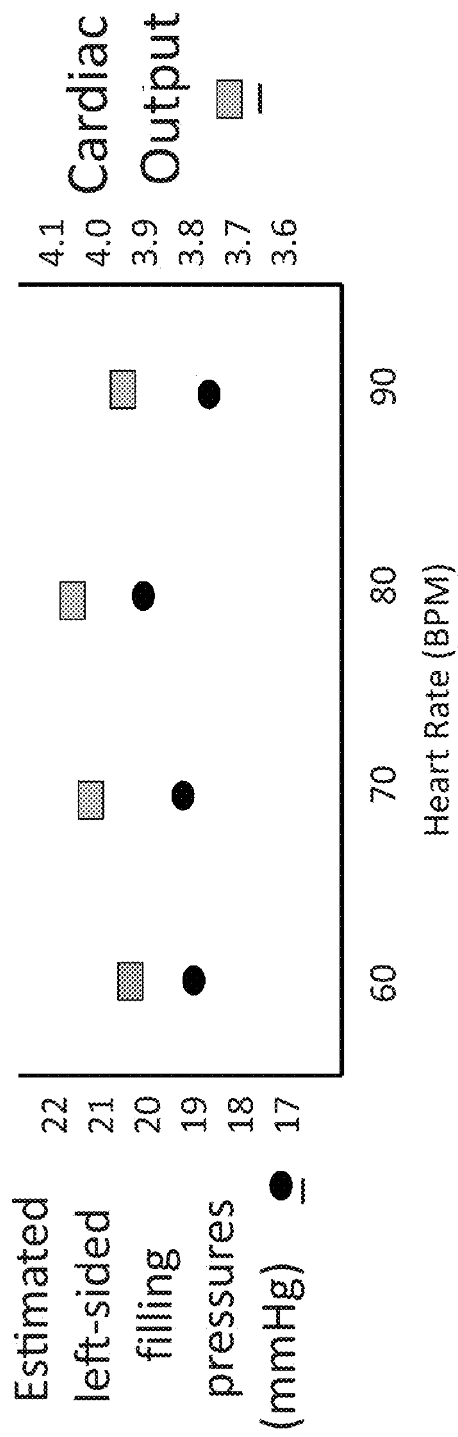
FIGS. 8A and 8B are graphs showing an example of how changes in heart rate and pressure differential affect both the estimated left-sided filling pressure and the cardiac output.
Figure 8B:
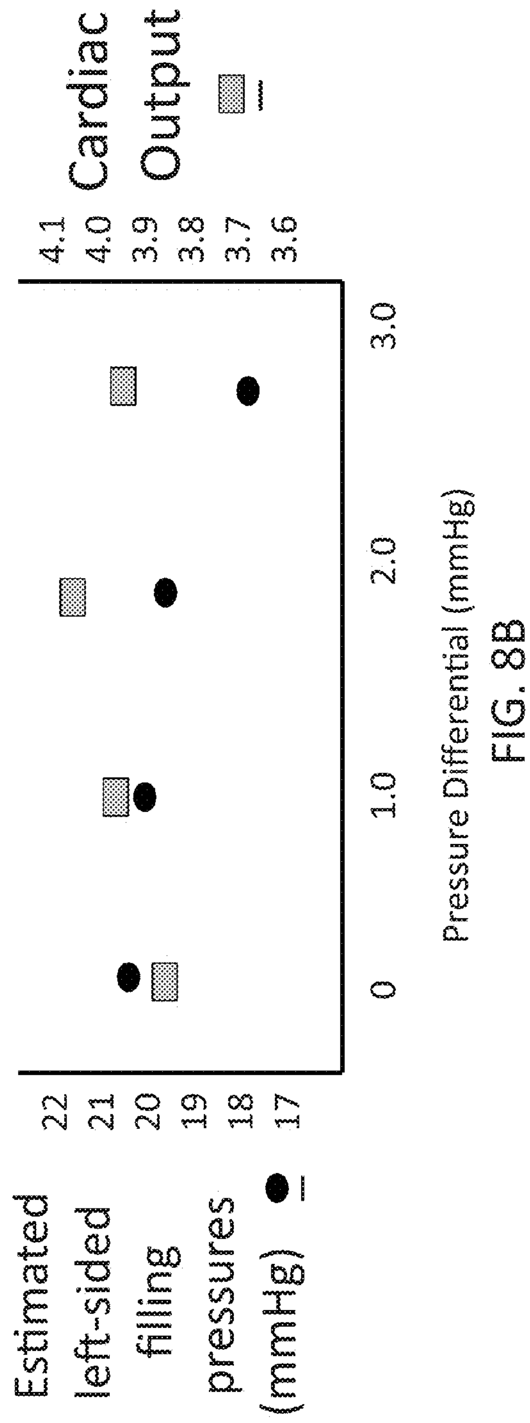

FIGS. 8A and 8B are graphs that show how slight changes in heart rate and the pressure differential may cause changes in both the estimate of left-sided filling pressures (in mmHg) and the cardiac output (in liters a minute). Both the heart rate and the pressure differential may be gradually changed over time, e.g., using the systems and methods described herein. With any change, a few minutes may be required in order for the body to create a new equilibrium, at which time the measurements may be recorded again. The combinations of heart rate and pressure differential may be gradually altered in order to create a series of relationships between the estimated left-sided filling pressures and cardiac output. This curve may be determined for various levels of patient activity. Once the optimal left-sided filling pressures to cardiac output is determined at the determined level of patient activity and total body blood volume, the required heart rate and pressure differential may be maintained.

Figure 9:
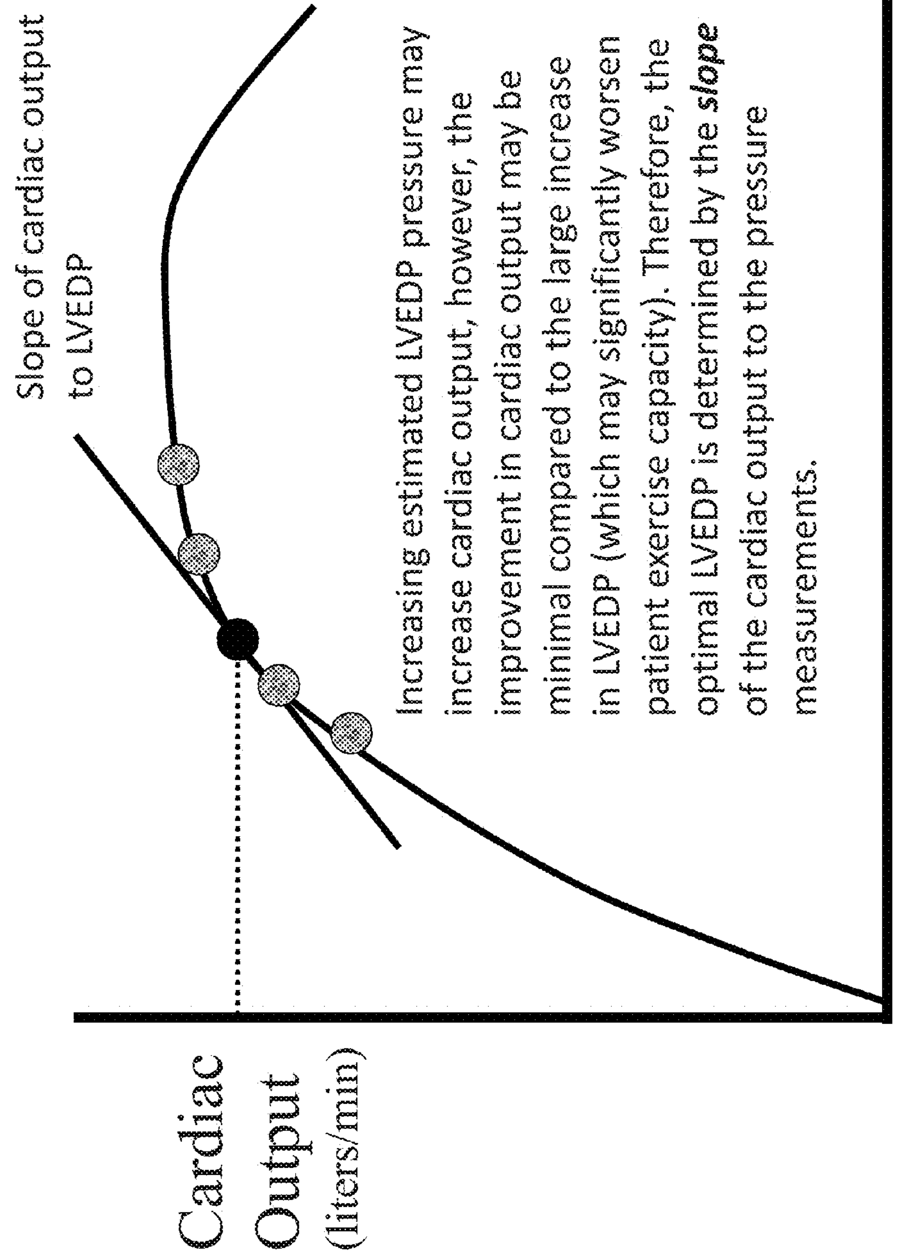
FIG. 9 is a graph showing the relationship between the estimated left sided filling pressures and estimates of cardiac output illustrating an exemplary method for using the slope of this relationship to determine the optimal heart rate and pressure differential.

FIG. 9 is a graph that illustrates an exemplary relationship between the measurements obtained in FIG. 5 at one level of patient activity and total body blood volume. As shown in FIG. 6, the estimated cardiac output may be determined for various estimates of the left-sided filling pressure and the left ventricular end diastolic pressure (LVEDP). The resulting curve shown in FIG. 9 is, in essence, the Frank-Starling curve for this patient's level of activity and volume status. Note that at lower pressures, an increase in LVEDP results in an increase in cardiac output. However, at some point, increasing LVEDP results in mild improvement in cardiac output. At high filling pressures, increasing the LVEDP even more may actually decrease cardiac output. Increasing the cardiac output may improve oxygen delivery to tissue and improve kidney function, which may help with diuresis in heart failure patients. However, the LVEDP that optimizes cardiac output may be significantly high to worsen respiratory status. Therefore, the slope relating the LVEDP to the cardiac output may be used to estimate the optimal LVEDP and cardiac output. The slope of the pressure/output curve may be adjusted and determined empirically by a controller of the system at various levels of patient exercise.

Figure 10:
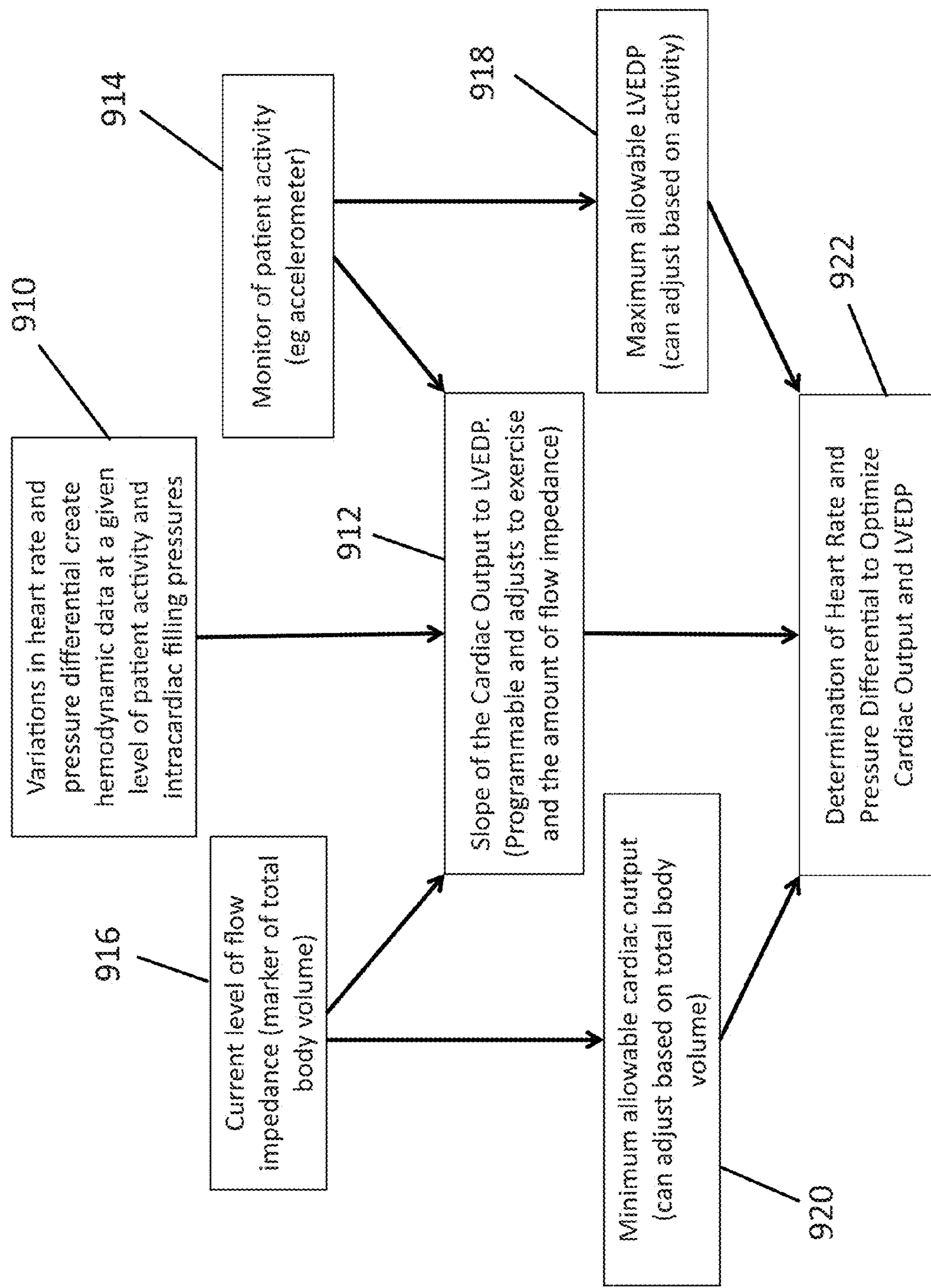
FIG. 10 is a flow chart showing an exemplary methods for determining the optimal heart rate and pressure differential based on measurements and programmable aspects of a system implanted within a patient's body.

Turning to FIG. 10, an exemplary method is shown for determining optimal heart rate and/or pressure differential, e.g., using any of the systems described elsewhere herein. The controller of the system may operate the flow impedance device and other components to enable the desired data to be acquired and calculations to be performed.

Variations in heart rate and pressure differential are used in order to estimate the relationship between left-sided filling pressures and cardiac output. For example, at step 910, heart and pressure differentials obtained using the system, e.g., across the flow impedance device 136 shown in FIG. 3, may generate hemodynamic data at a given level of patient activity and intracardiac filling pressures. At step 912, the controller may then use the slope of this relationship (e.g., as demonstrated in FIG. 9) to determine the optimal left-sided filling pressure and cardiac output.

Optionally, at step 914, an accelerometer implanted in the patient's body, e.g., within the housing 142 of the controller 140 shown in FIG. 2, may be used to identify the patient's level of activity. For example, the controller 140 may acquire data from the accelerometer indicating that the patient is resting (e.g., no substantially signals from the accelerometer) or active (or the controller 140 may determine various levels of activity based on the signals from the accelerometer). In addition, at step 916, the controller 140 may identify the current level of flow impedance from the flow impedance device 136, which may provide an estimate of the total body volume of the patient.

At step 918, the controller 140 may also determine the maximum allowable left-sided filling pressure and minimum cardiac output allowable. These values may also be dependent on the level of patient activity and the total body blood volume. That is, when the patient is at an increased level of activity, the controller may accept a higher maximum of left-sided filling pressure. At step 920, when the patient has an increased level of total body volume (as evidenced by a high pressure differential), the minimum cardiac output may be raised in order to encourage diuresis. At step 922, these values are then incorporated into the algorithm generated by the controller and used to determine the optimal heart rate and pressure differential, e.g., to optimize cardiac output and/or left ventricular end diastolic pressure (LVEDP).

Once calibrated, pressure differential and heart rate may be anticipated based on patient activity and intracardiac pressures in order to optimize filling pressures and/or cardiac output. Over time, the decreased left atrium and left ventricle filling pressures may lead to beneficial myocardial remodeling. This may improve myocardial function and/or decrease arrhythmias and/or ectopic beats.

As a result of the systems and methods herein, diastolic and systolic function may improve over time. Furthermore, device pacing and pressure control algorithms may be developed to accelerate this process (similar to how exercise is known to improve diastolic dysfunction).

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system to be implanted in the body of a patient with conduction disease and/or heart failure configured to monitor and/or treat the patient, the system comprising:

at least one sensor configured to provide sensor data corresponding to pressures within or near the patient's heart;

an elongate member comprising a proximal end and a distal end sized for introduction into a venous side of a patient's heart;

an adjustable component carried on the distal end and configured to be positioned within a body lumen of the venous side of the patient's heart, the adjustable component being adjustable to create a pressure gradient to blood flow within the venous side of the patient's heart;

at least one pacing component configured to at least one of sense and pace the patient's heart; and a controller contained within a housing sized for implantation within the patient's body adjacent the heart, the proximal end of the elongate member coupled to the housing, the controller coupled to the at least one pacing component and the adjustable component, the controller programmed to adjust the adjustable component based at least in part on sensor data from the at least one sensor to generate a pressure gradient within the venous side of the patient's heart to reduce intracardiac filling pressures within the patient's heart.

2. The system of claim 1, further comprising at least one additional sensor configured to provide sensor data corresponding to the stroke volume or cardiac output of the patient's heart.

3. The system of claim 2, further wherein the at least one additional sensor comprises a plurality of electrodes configured to measure changes in electrical impedance that correlate with changes in blood volume.

4. The system of claim 3, wherein the controller is coupled to the plurality of electrodes and configured to estimate cardiac output of the patient's heart by measuring the changes in electrical impedance from the plurality of electrodes.

5. The system of claim 1, wherein the at least one adjustable component comprises an annular flow impedance device implantable within a patient's inferior vena cava, the flow impedance device including a flow passage to allow blood flow through the inferior vena cava into the patient's heart, and wherein the controller is programmed to actuate the flow impedance device to constrict or open the flow passage to induce a pressure gradient across the flow impedance device.

6. The system of claim 1, wherein the adjustable component is carried on the distal end of the elongate member proximal to a distal tip of the elongate member.

7. The system of claim 6, wherein the at least one sensor comprises a sensor adjacent the distal tip of the elongate member distal to the adjustable component.

8. The system of claim 1, wherein the controller is programmed to adjust the adjustable component at a rate substantially slower than the patient's heart rate.

9. The system of claim 1, wherein the controller is programmed to reduce intracardiac filling pressures while increasing cardiac output of the patient's heart.

10. A method for treating a patient with conduction disease and/or heart failure configured to monitor and/or treat the patient, comprising:

introducing a distal end of an elongate member into a venous side of a patient's heart, the distal end carrying at least one sensor configured to provide sensor data corresponding to pressures within or near the patient's heart and an adjustable component configured to create a pressure gradient to blood flow within or near the patient's heart;

manipulating the elongate member to position the adjustable component within a body lumen of the venous side of the patient's heart;

introducing at least one pacing component into or adjacent the patient's heart;

implanting a housing containing a controller within the patient's body adjacent the heart; and coupling the controller to the at least one sensor and the adjustable component;

wherein the controller is programmed to adjust the adjustable component based at least in part on sensor data from the at least one sensor to create a desired pressure gradient to blood flow within the patient's heart to reduce intracardiac filling pressures within the patient's heart.

11. The method of claim 10, wherein the adjustable component comprises an expandable member, wherein manipulating the elongate member comprises positioning the expandable member within one of the patient's inferior vena cava and the right atrium of the patient's heart, and wherein adjusting the adjustable component comprises at least partially expanding or changing a shape of the expandable member to generate the pressure gradient to blood flow.

12. The method of claim 10, wherein the adjustable component is adjusted to induce a reduction in filling pressures within a left chamber of the patient's heart.

13. The method of claim 10, wherein the adjustable component is positioned within an inferior vena cava of the patient's heart, the controller programmed to adjust the adjustable component to create a pressure gradient in the inferior vena cava that moves extraneous and congesting fluid to vessels upstream from the inferior vena cava.

14. The method of claim 10, wherein the adjustable component is positioned within the inferior vena cava, the controller programmed to adjust the adjustable component to create a pressure gradient in the inferior vena cava to modify left-side filling pressures within the patient's heart.

15. The method of claim 10, wherein the adjustable component comprises an annular flow impedance device carried on the distal end of the elongate member, wherein manipulating the elongate member comprises positioning the flow impedance device within the patient's inferior vena cava such that a flow passage through the flow impedance device allows blood flow through the inferior vena cava into the patient's heart, and wherein adjusting the adjustable component comprises actuating the flow impedance device to constrict or open the flow passage to induce a pressure gradient across the flow impedance device.

16. The system of claim 10, wherein the controller is programmed to adjust the adjustable component to reduce intracardiac filling pressures and simultaneously control the at least one pacing component to modify a heart rate of the patient in order to create a desired pressure-cardiac output relationship.

17. The method of claim 10, wherein the body lumen within which the adjustable component is positioned is one of an inferior vena cava, a superior vena cava, a right atrium, and a right ventricle of the patient's heart.

18. The method of claim 10, wherein the controller is programmed to adjust the adjustable component independent of heart beat.

19. The method of claim 10, wherein the controller is programmed to adjust the adjustable component at a rate substantially slower than the patient's heart rate.

20. A method for treating a patient with conduction disease and/or heart failure, the method comprising:

implanting a controller contained within a housing within a patient's body adjacent the patient's heart;

coupling a proximal end of an elongate member to the housing;

introducing a distal end of the elongate member into one of a venous vessel or the patient's heart to position adjustable component carried on the distal end within one of the patient's inferior vena cava and a right atrium of the patient's heart, the elongate member comprising at least one sensor for providing pressure data adjacent to the adjustable component; and coupling the controller to the adjustable component and the at least one sensor, the controller programmed to adjust the adjustable component based at least in part on pressure data from the at least one sensor to create a desired pressure gradient to blood flow within the patient's heart, thereby reducing intracardiac filling pressures without reducing cardiac output of the patient's heart.

21. The method of claim 20, wherein the at least one adjustable component comprises an expandable member, the distal end of the elongate member is introduced into the patient's heart to position the expandable member within the right atrium, the controller programmed to selectively expand the expandable member to at least partially fill the right atrium to create the desired pressure gradient.

22. The method of claim 20, wherein introducing the distal end of the elongate member comprises positioning the at least one adjustable component within the inferior vena cava, the controller programmed to adjust the at least one adjustable component to partially impede flow through the inferior vena cava to create the desired pressure gradient.

23. The method of claim 22, wherein the at least one adjustable component comprises an annular flow impedance device including a flow passage that allow blood flow through the inferior vena cava into the patient's heart, and wherein the controller is programmed to actuate the flow impedance device to constrict or open the flow passage to induce a pressure gradient across the flow impedance device.

* * * * *